United States Patent [19]
Grandon

[11] Patent Number: 4,739,761
[45] Date of Patent: Apr. 26, 1988

[54] CORNEA MARKER

[76] Inventor: Stanley C. Grandon, 4529 Tanbark, Bloomfield Hills, Mich. 48013

[21] Appl. No.: 878,641

[22] Filed: Jun. 26, 1986

[51] Int. Cl.⁴ ............................................. A61B 17/32
[52] U.S. Cl. .................................. 128/305; 128/303 R
[58] Field of Search ..................... 128/305, 310, 305.1, 128/303 R

[56] References Cited

U.S. PATENT DOCUMENTS 4,357,941 11/1982 Golubkov et al. .................. 128/316
4,417,579 11/1983 Soloviev et al. ................ 128/305 X

FOREIGN PATENT DOCUMENTS 854383 8/1981 U.S.S.R. .............................. 128/305

Primary Examiner—Michael H. Thaler
Attorney, Agent, or Firm—Krass & Young

[57] ABSTRACT

Cornea marker apparatus and a method of corneal marking are provided for purposes of corrective surgery. The apparatus features a blade assembly having readily visible blade ends as well as a blade assembly concept with a radial guide allowing rotation of the blades to selected meridian alignments for precise marking of the surface of the cornea.

13 Claims, 2 Drawing Sheets

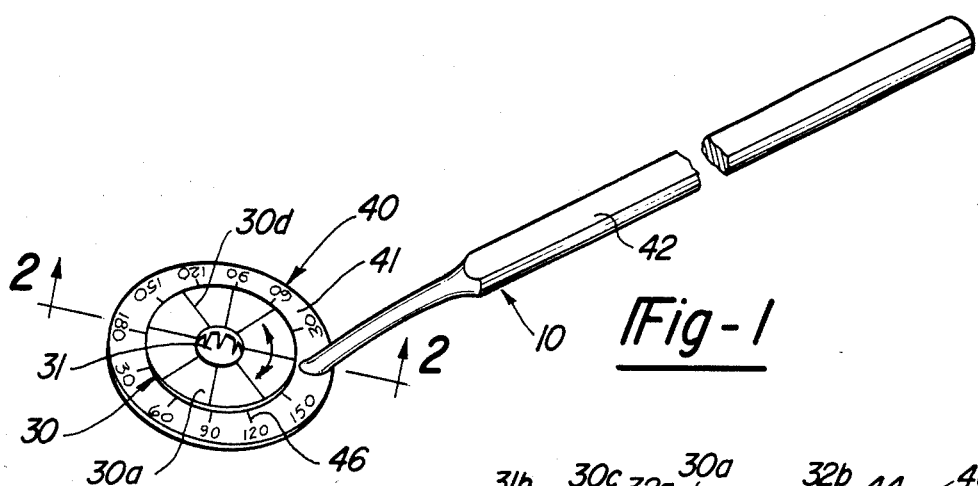

CORNEA MARKER

TECHNICAL FIELD

This invention relates to eye surgery and more particularly to cornea marker apparatus and means of marking for corrective surgery such as radial and chordal refractive keratotomy (RK).

BACKGROUND ART

For the functional correction of eye disorders such as myopia and astigmatism due to abnormal curvature of the central clear zone of the cornea of the eye, a refractive keratotomy procedure provides benefit. In this procedure, for restoration of a flat clear zone, based on pre-operative patient selection and measurement of visual parameters such as corneal thickness, the cornea is first marked in a predetermined radially balanced pattern by making a circular cut (cf. U.S. Pat. No. 4,357,941) or a series of shallow incisions (cf. U.S. Pat. No. 4,417,579) in the annular corneal surface surrounding the clear zone. Visualization of the incisions is facilitated by delineation with a suitable dye such as fluorescein or gentian violet. The marking is done by free hand marking or preferably by a hand-held radial marker instrument of conventional spider-wheel design. One commercially available marker of this design is described in the work by Sanders et al. entitled "Radial Keratotomy," pages 31 and 32, 1984, Slack Inc., Thorofare, N.J.

The marking procedure is then followed first by corneal thickness measurements (pachymetry) and then by making refractive incisions on the marked pattern of lines, using a diamond knife.

The prior art method of free hand marking often is unreliable whereas the method employing a spider-wheel marker tends to be unreliable in certain particulars. One problem, not generally recognized as important, is that the ends of each blade edge are not readily visible, and especially the inner end is not visible for purposes of centration and spacing from the clear zone. Another problem of the kind is that the marker lacks means for correctly and reliably aligning the marker to the corneal surface of an eye with astigmatism, for example, astigmatism with the rule where the vertical meridian has the greater curvature, or astigmatism against the rule where the horizontal meridian has the greater curvature, or irregular astigmatism due to uneven bulges, corneal scarring and the like.

It is therefore an object of the present invention to provide improved cornea marker apparatus having marker blades that are conspicuous for purposes of concentric placement and spacing from the central clear zone of the corneal surface.

It is another object of the invention to provide improved cornea marker apparatus having a marker blade assembly holder and a rotary blade assembly that can be controllably rotated in the holder to achieve correct placement for radially marking selected meridians of the corneal surface.

It is still another object of the invention to provide apparatus of the kind described in which the rotary blade assembly can be replaced in the holder with a different rotary blade assembly that may differ in shape, size, or radial orientation of the blades.

It is yet another object to provide improved methods for marking the corneal surface for purposes of corrective surgery.

These and other objects, features and advantages will be seen from the following description and accompanying drawings.

DISCLOSURE OF THE INVENTION

The invention in one preferred aspect concerns improved surgical apparatus for concentric placement on the cornea of the eye and for radially marking selected meridians of the corneal surface surrounding the central clear zone of the eye. The apparatus comprises a circumferential support frame having a central opening dimensioned for concentric alignment exposing the clear zone, and a pair of diametrically opposed co-planar radially disposed knife blades for each of said selected meridians. Each blade has a cutting edge with concave curvature adapted in 3-dimensioned blade assembly profile for co-extensive matching contact with the convex curvature of the outer corneal surface. Also, each blade is unitary with and supported on the support frame with its inner blade end projecting into the central opening whereby the blade inner ends are conspicuously exposed in the support frame opening for enabling precise placement of the blades in the corneal field. Preferably, the opening in the support frame is circular or elliptical.

In a preferred embodiment, the apparatus comprises a blade assembly holder and a rotary knife blade assembly. The holder has a central opening and a concentric circumferential bearing surface for engagement with the bearing surface of the rotary knife blade assembly.

The knife blade assembly includes a circumferential support frame having a central opening, preferably circular or elliptical, dimensioned for concentric alignment exposing the clear zone, and a pair of diametrically oppose co-planar radially disposed knife blades for each of the meridians selected for marking. Each blade has a cutting edge with concave curvature adapted in profile for co-extensive matching contract with the convex curvature of the outer corneal surface. Each blade is unitary with and supported on the support frame, the assembly being configured with a peripheral bearing surface adapted for engagement with said concentric bearing surface and allowing rotation with respect to the blade holder. Preferably, the inner end of each blade is conspicuously exposed in the support frame opening. Preferably, the knife blade assembly comprises blade guide indicia coinciding with the diametral alignment of each blade pair.

In a preferred embodiment, the blade holder comprises meridial indicia referable to the degree of rotation of a rotary knife blade assembly contained in the blade holder. In another preferred embodiment, the support frame is elliptical and the cutting edges of the blades of the knife blade assembly are configured with a 3-dimensional concave elliptical curvature for coextensive matching contact with the convex curvature of an ellipitcal astigmatic outer corneal surface. The blade assembly holder and the rotary blade assembly in a preferred embodiment are adapted to be removably fitted together, preferably in a snap fit, to a position for controlled rotation of the blade assembly to predetermined positions for marking of selected meridians. The holder and rotary blade assembly preferably are adapted to be disengageable for replacement of a different rotary blade assembly in the blade assembly holder.

The invention in another preferred aspect concerns an improved method for marking selected meridians of the outer corneal surface surrounding the open central zone of the cornea of the eye. The eye to be treated may be astigmatic, having greater curvature in a meridian that may be a vertical, horizontal, or other meridian. The method includes the step of providing a blade assembly holder with meridial indicia and a rotary knife blade assembly that is rotatable in the holder. The knife blade assembly has a marking surface substantially matching the outer corneal surface. The assembly has a predetermined pattern, circular or preferably elliptical, of opposed knife blade edges aligned in a pair for placement across the open corneal zone for each of the selected meridians. The method further comprises placing the knife blade edges of the marking surface in a selected meridian alignment with the corneal surface, and marking the cornea by knife edge cutting sufficient for visualization of the resulting meridial incisions. In a preferred embodiment, the blade assembly comprises blades having the curvature of about 47 diopters.

BRIEF DESCRIPTION OF THE DRAWINGS

The invention will be more fully understood by reference to the following detailed description and accompanying drawings in which:

FIG. 1 is a perspective view partly segmented of a preferred cornea marker according to the invention;

FIG. 2 is a cross-sectional view taken on line 2—2 of FIG. 1 showing the marker blade curvature in relation to curvature of the cornea of the eye;

FIG. 3 is an exploded view similar to the view of FIG. 1;

FIGS. 4 to 7 are plan views illustrating different preferred patterns of radially disposed paired marker blades of a cornea marker according to the invention;

DETAILED DESCRIPTION OF THE PREFERRED EMBODIMENTS

Figure 8:
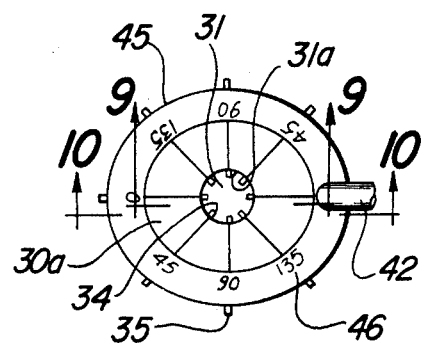
FIG. 8 is a plan view of another preferred embodiment illustrating an elliptically disposed marker blade assembly with exposed inner and outer blade ends.
Figure 9:
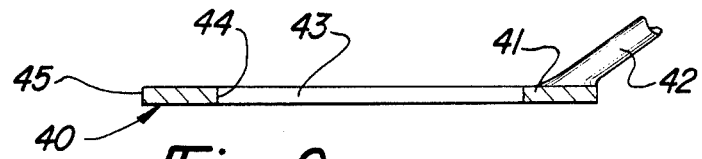
FIG. 9 is a side view of a blade assembly holder in section taken on line 9—9 of FIG. 8.
Figure 10:
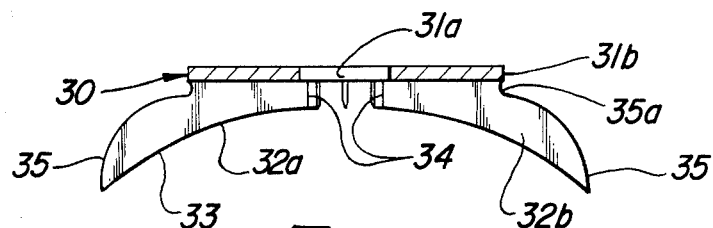
FIG. 10 is a side view of paired marker blades on a frame support partly in section taken on line 10—10 of FIG. 8.
Figure 11:
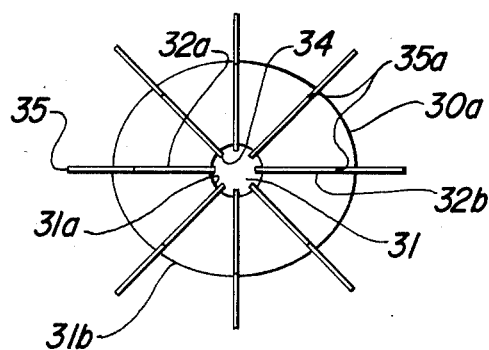
FIG. 11 is a bottom view of the marker blade assembly of FIG. 8.

In the embodiment of FIG. 1 a cornea marker 10 is shown with a marker blade assembly 30 having a blade support frame 30a in the form of an annular cap. As seen in FIG. 2, the frame or cap 30a carries on its underside a pattern or array of edge-mounted radially disposed knife blade pairs 32a and 32b. The frame has a central opening 31 with inner and outer edges 31a,31b. The frame also has a circumferential skirt 30b depending from its underside that together define a circumferential skirt groove 30c. The top side of the frame carries blade alignment indicia 30d. As seen in FIG. 2, the blades have a cutting edge 33 with concave curvature terminating at an inner end 34 and an outer end 35. In relation to the surface of the cornea 20 for purposes of marking, the cutting edges of the blade pair 32a,32b are located for concentric placement in co-extensive matching contact with the corneal surface. The inner edges 34 of the blades are spaced from the clear zone 21 while the outer edges 35 are spaced away from the corneal limbus 22. Also as seen in FIG. 2, the blade assembly is supported for rotation in a holder 40 having an annular base plate 41 carried for manipulation by a handle 42. The base plate has meridian indicia 46 on its upper face and has inner and outer edges 44,45 and the inner edge defining a circular opening and being configured for engagement with the skirt groove 30c, also circular. In a preferred embodiment, the two parts 30 and 40 are constructed such that they can be assembled together and disassembled (as shown in FIG. 3), as desired, preferably by means of a snap fit allowing relative rotation as between the two parts. When the blade assembly 30 is rotated, the same can be advanced to any desired position for marking by setting the blade alignment indicia 30d to coincide with the meridian indicia 46 requiring marking, such as the vertical (90°) meridian or the horizontal (0° or 180°) meridian. Different patterns of marking can be achieved by using any of the different blade configurations shown in FIGS. 4 to 7. A preferred embodiment of the cornea marker is illustrated in FIG. 8. The blase assembly 30 has a circumferential groove 35a that is circular and the holder 40 has an inner edge 44 defining a matching central opening 43 so that when assembled the two parts can be rotated relative to each other. The blade assembly has an annular cap 30a that is elliptical with an elliptical central opening 31. The blade pairs are secured to the cap 30a by suitable means such as welding and are arranged with their inner and outer ends 34,35 open to view for precise placement and marking when held in the operative position shown in FIG. 8.

In operation, by marking methods which will be understood by those skilled in eye surgery, a blade assembly of the invention is selected that provides the most suitable pattern of marking for the particular surgical procedure, whether for correction of myopia, astigmatism or a combination of these. The appropriate blade assembly and the holder are assembled, and the assembly is rotated if necessary to the desired meridial alignment, for example the alignment shown in FIG. 8 for a marking pattern to correct for astigmatism. The marker is then placed in a marking position such as that shown in FIG. 2 (with the long axis blade pair on the horizontal meridian), and the corneal surface surrounding and adjacent to the clear zone is marked for purposes of pachymetry and refractive keratotomy.

What is desired to claim as my exclusive property in the invention, as described, is the following.

I claim:

1. Surgical apparatus for concentric placement on the cornea of the eye and for radially marking selected meridians of the corneal surface surrounding the central clear zone of the eye, comprising:

a planar blade assembly holder plate having a central opening and a concentric circumferential bearing surface, for engagement with the bearing surface of a rotary knife blade assembly, a rotary knife blade assembly including a planar circumferential support frame having a central opening dimensioned for concentric alignment exposing the clear zone, and a pair of diametrically opposed co-planar radially disposed knife blades for each of said selected meridians, each blade having a cutting edge with concave curvature adapted in profile for co-extensive matching contact with the convex curvature of the outer corneal surface, and each blade further being unitary with and supported on the support frame, the assembly being configured with a circular peripheral bearing surface engaging said concentric bearing surface by a snap fit allowing rotation of the assembly planar frame in parallel relation with respect to the planar blade holder plate.

2. Surgical apparatus according to claim 1 where the opening in the support frame is circular.

3. Surgical apparatus according to claim 1 where the opening in the support frame is elliptical.

4. Surgical apparatus according to claim 2 where the inner end of each blade is conspicuously exposed in the support frame opening.

5. Surgical apparatus according to claim 3 where the inner end of each blade is conspicuously exposed in the support frame opening.

6. Surgical apparatus according to claim 1 where the knife blade assembly comprises blade guide indicia coinciding with the diametral alignment of each blade pair.

7. Surgical apparatus according to claim 1 where the blade holder plate comprises meridial indicia referable to the degree of rotation of a rotary knife blade assembly contained in the blade holder.

8. Surgical apparatus according to claim 1 where the support frame is elliptical and the cutting edges of blades of the knife blade assembly are configured with a 3-dimensional concave elliptical curvature for co-extensive matching contact with the convex curvature of an elliptical astigmatic outer surface.

9. Surgical apparatus according to claim 4 where the blade assembly holder plate and the rotary blade assembly are adapted to be reversibly fitted together to a position for controlled rotation of the blade assembly to predetermined positions for marking of selected meridians.

10. Surgical apparatus according to claim 9 where the blade assembly holder plate and the roatry blade assembly are adapted to be fitted together in a snap fit and to be reversibly disengageable for replacement of a different rotary blade assembly in the blade assembly holder.

11. Surgical apparatus according to claim 9 where the rotary blade assembly is circular.

12. Surgical apparatus according to claim 9 where the rotary blade assembly is elliptical.

13. Surgical apparatus according to claim 9 where the inner end of each blade is conspicuously exposed in the support frame opening.

* * * * *